US00PP19825P3

(12) United States Plant Patent
Brauns

(10) Patent No.: US PP19,825 P3
(45) Date of Patent: Mar. 17, 2009

(54) **VARIETY OF *CORDYLINE* PLANT 'BRA01'**

(50) Latin Name: *Cordyline fruiticosa*
Varietal Denomination: BRA01

(76) Inventor: Peter Brauns, 22 Pyne Street, Edmonton, Queensland (AU), 4869

( * ) Notice: Subject to any disclaimer, the term of this patent is extended or adjusted under 35 U.S.C. 154(b) by 1 day.

(21) Appl. No.: 10/929,291

(22) Filed: Aug. 30, 2004

(65) Prior Publication Data

US 2006/0048257 P1 Mar. 2, 2006

(30) Foreign Application Priority Data

Apr. 15, 2004 (AU) ..... 2004/133

(51) Int. Cl.
*A01H 5/00* (2006.01)

(52) U.S. Cl. ..... Plt./383
(58) Field of Classification Search ..... Plt./373, Plt./383
See application file for complete search history.

(56) References Cited

U.S. PATENT DOCUMENTS

| | | | | | |
|---|---|---|---|---|---|
| PP8,800 | P | * | 6/1994 | van der Velden | Plt./383 |
| PP9,221 | P | * | 7/1995 | DeRoose | Plt./370 |
| PP14,224 | P3 | | 10/2003 | Jury et al. | |
| 2006/0048257 | P1 | * | 3/2006 | Brauns | Plt./373 |

OTHER PUBLICATIONS http://www.monoviastyle.com/monroviaweb.nsf/8c104835579b67e18825685f006acdf8/6fde8e21c9ccd7ff85256f38007eb021!OpenDocument.*

UPOV ROM GTITM Computer Database, GTI Jouve Retrieval software Mar. 2005 citations for 'BRA01' and Corbra.*

* cited by examiner

*Primary Examiner*—Wendy C. Haas
(74) *Attorney, Agent, or Firm*—Fulwider Patton LLP

(57) ABSTRACT

A new and distinct cultivar of *Cordyline* plant named 'BRA01' characterized by a small clump forming growth habit with deep purple-black foliage and a relatively short internodal space.

1 Drawing Sheet

Botanical designation: *Cordyline fruiticosa.*
Variety Denomination: 'BRA01'.

BACKGROUND OF THE NEW PLANT

The present invention relates to a new and distinct cultivar of *Cordyline* plant, botanically known as *Cordyline fruiticosa* and further known by the varietal name 'BRA01'. This new variety is also sold under the trade name CARUBA BLACK. The new variety was created from a sport of a wild green *Cordyline fruiticosa* (RHS 141A (1995)) collected by Michael Yappi in the Western Highlands region of New Guinea in Mt. Hagen. The sport was then provided to a plant collector, Michael Ferrero of Cairns, Queensland Australia, and imported to plant breeder Peter Brauns of Plant Source Australia who performed further trials and selections using vegetative reproduction techniques in a cultivated area. The parental cultivar is a green leaved *Cordyline fruiticosa* (unpatented). The new variety has purple/black foliage. The cuttings were planted out and plants with desirable ornamental characteristics were selected. The cultivar was isolated by the inventor in Australia by selecting primarily on the basis of compact growth habit, foliage color, and suitability as a garden or container grown plant.

Following selection of the plant, the cultivar was propagated vegetatively through cutting and division at Edmonton, Queensland, Australia. Continued observation of the vegetative divisions resulting from asexual reproduction taken at Edmonton, Queensland, Australia have confirmed that the distinguishing features of this new cultivar came true, remain stable and are retained through successive propagation.

The closest comparator to 'BRA01' known to applicant is *Cordyline fruiticosa* 'Hawaiian Flag' (unpatented) which is a clump forming plant with green foliage and some purple and yellow variegations, a mean width of 92 mm, and a mean length of 389 mm excluding the petiole. The parent wild green *C. fruiticosa* has green foliage and a plant size up to 1.8 meters.

SUMMARY OF THE INVENTION

Plants of the cultivar 'BRA01' have not been observed under all possible environmental and cultural conditions. The phenotype may vary somewhat with variations in environment such as temperature, light intensity, length of day, irrigation amount and frequency, and/or fertilizer rate without, however, any variance in genotype.

The following traits have been repeatedly observed and are determined to be among the unique characteristics of 'BRA01'. These characteristics distinguish 'BRA01' as a new and distinct cultivar from its closest comparator *Cordyline fruiticosa* 'Hawaiian Flag':

1. Purple-black leaves with deep green hues;
2. Compact growth habit up to 1.2 meters;
3. Shorter leaf length;
4. Smaller leaf width; and
5. Shorter internodal space.

Compared to other plants of the *Cordyline* genus, the new *Cordyline* has a distinctive foliage with purple-black leaves having deep green hues.

BRIEF DESCRIPTION OF THE DRAWINGS

The invention is depicted in the accompanying colored photographs in which.

Figure 1:
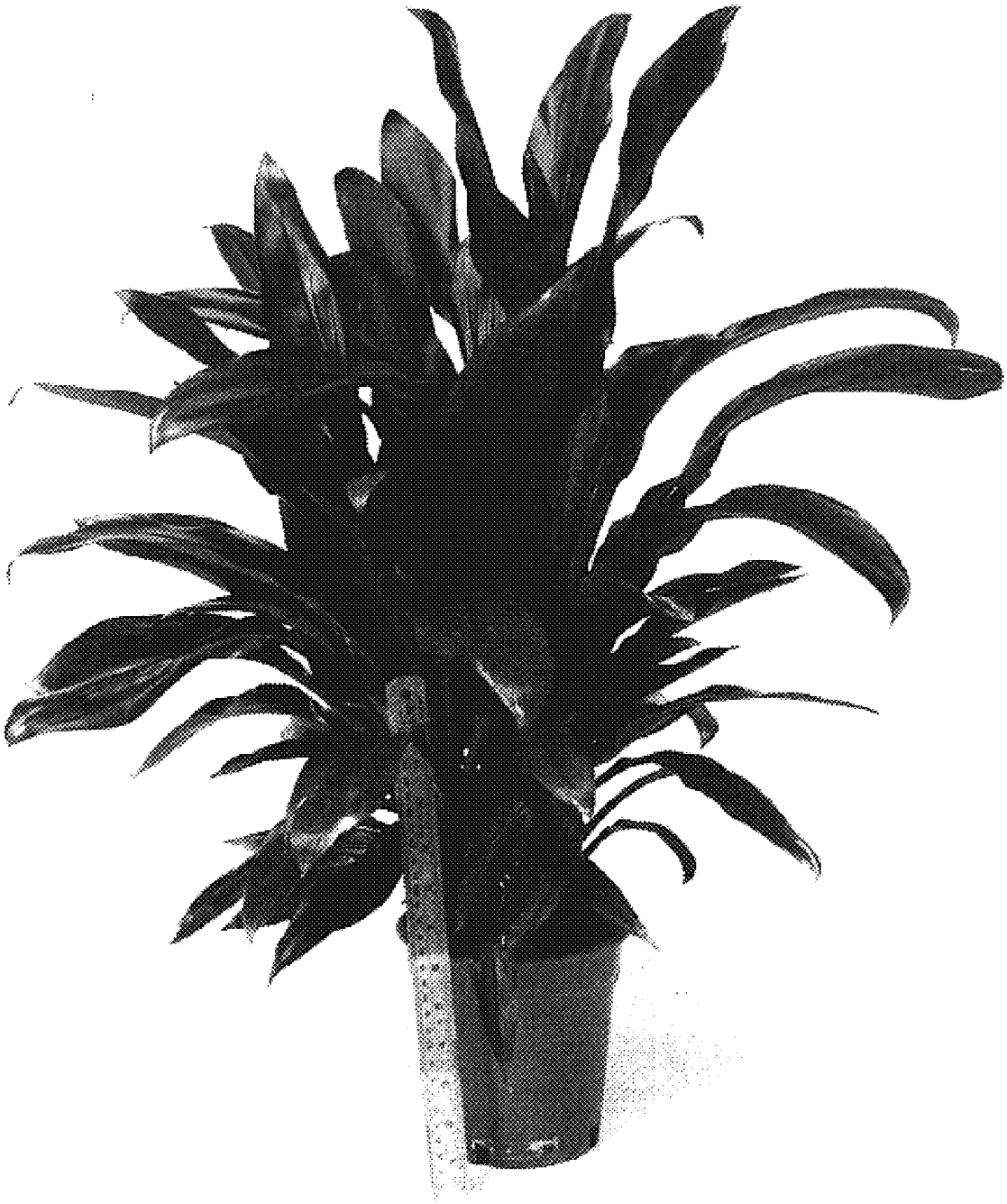
FIG. 1 shows a potted plant illustrating the characteristic foliage.

The photograph depicts the overall appearance of the new *Cordyline,* showing the colors as true as it is reasonably possible to obtain in colored reproductions of this type. Colors in the photograph may differ slightly from the color values cited in the Detailed Botanical Description which more accurately describe the actual colors of the new *Cordyline.*

DETAILED BOTANICAL DESCRIPTION OF THE NEW PLANT

The following detailed description sets forth characteristics of the new cultivar. The data which defines each characteristic was collected from asexual reproductions of the plant grown in an open greenhouse with irrigation provided by drip feeding in a hydroponic system, and carried out by the observer at Edmonton, Queensland, Australia. The plant histories of *Cordyline* 'BRA01' were taken on 2 pots with 3 plants each and taking place in approximately January 2004 through June 2004.

In the following table of plant characteristics, color references are made to The Royal Horticultural Society of London Colour Chart, 1995 Edition. The measurements were taken from mature leaves.

THE PLANT

Classification:

*Botanical.*—*Cordyline fruiticosa.*
*Varietal name.*—'BRA01'.
*Parentage.*—Sport of wild green *Cordyline fruiticosa.*
*Asexual propagation.*—Root division and cuttings.

Form:

*Plant growth rate.*—Moderate.
*Growth habit.*—Upright, clumping, and compact.
*Plant density.*—Bushy.
*Growth type.*—Clumping.
*Mean plant height.*—650 mm.
*Mean plant width.*—550 mm.

Stem:

*Mean internode length.*—17.4 mm (taken below bulge where leat starts to bulge).
*Color.*—Brown to burgundy (c.a. RHS 200A, 1995).
*Mean stem diameter.*—9.75 mm.

Leaves:

*Leaf color.*—Leaf upper side brown to burgundy (c.a. RHS 200A, 1995) and leaf lower side brown to burgundy (c.a. RHS 200A, 2005).
*Leaf shape.*—Petiolate with lobed leaves and a wedge shaped base.
*Mean leaf width* (*mm*).—69.6 mm.
*Mean leaf length* (*mm*).—286 mm (excluding petiole).
*Leaf characteristics.*—Apex — V-shaped. Margin — Slight undulations. Texture — Smooth, semi-glossy. Shape — Lobed with a long petiole.
*Petiole mean length.*—105.86 mm.
*Petiole mean width.*—18.62 mm.
*Petiole shape.*—Curves upward, not joining.
*Petiole color* (*inside*).—144B.
*Petiole color* (*outside*).—200B with a Burgundy hue.

Inflorescence: May not flower in temperate zones.

GENERAL CHARACTERISTICS

'BRA01' is primarily distinguished from other cultivars of *Cordyline* genus by its purple-black foliage, compact growth habit, and shorter internodal space. 'BRA01' is a bushy clump forming plant with an upright compact growth habit wherein the leaves are petiolate and lobed with a smooth, semi-glossy texture and slight undulations on their margins.

What is claimed is:

1. A new and distinct *Cordyline fruticosa* plant named 'BRA01' substantially as illustrated and described.

* * * * *